(12) United States Patent
Mayr (10) Patent No.: US 6,805,870 B1
(45) Date of Patent: Oct. 19, 2004

(54) PARAMUNITY INDUCER BASED ON COMBINATIONS OF POXVIRUS COMPONENTS, PROCESS TO PREPARE IT AND ITS USE AS MEDICAMENT

(76) Inventor: Anton Mayr, Bockmeyrstrasse 9, D-80992 München (DE)

( * ) Notice: Subject to any disclaimer, the term of this patent is extended or adjusted under 35 U.S.C. 154(b) by 0 days.

(21) Appl. No.: 08/693,052

(22) PCT Filed: Jan. 17, 1995

(86) PCT No.: PCT/EP95/00160

§ 371 (c)(1),
(2), (4) Date: Aug. 20, 1996

(87) PCT Pub. No.: WO95/22978

PCT Pub. Date: Aug. 31, 1995

(30) Foreign Application Priority Data

Feb. 23, 1994 (DE) .......................................... 44 05 841

(51) Int. Cl.[7] ............................................. A61K 39/275
(52) U.S. Cl. ................ 424/281.1; 424/93.6; 424/232.1; 435/236; 435/238
(58) Field of Search ........................... 424/278.1, 204.1, 424/211.1, 214.1, 215.1, 232.1, 218.1, 281.1, 282.1, 93.6; 435/236, 238, 948

(56) References Cited

U.S. PATENT DOCUMENTS 5,094,850 A * 3/1992 Mayr et al. .................... 424/89

OTHER PUBLICATIONS

Pincus et al. "Poxvirus–Based Vectors as Vaccine Candidates". Biologicals. vol. 23, pp 159–164, 1995.*
Erfle et al. "The influence of paramunisation, Tumor Cell Vaccination and Whole Body Irradiation on the Growth of Radiation–induced Murine Osteosarcoma". Zbl. Vet. Med. B., vol. 30, pp 36–47, 1983.*
Brunecker et al. "Comparison of the Effect of Viral Paraimmunity Inducers PIND–AVI and PIND–ORF with that of BCG, Corynebacterium pavum and Levamisole on the Growth of Radiation–Induced Murine Osteosarcoma," J. Vet. Med. B., vol. 33, pp 188–195, 1986.*

Goldstein et al. "Effect of Formalin, B–Propiolactone, Methiolate and Ultraviolet Light Upon Influenza Virus Infectivity, Chicken Cell Agglutination, Hemagglutination, and Antigenicity." Applied Microbiology. vol. 19, No. 2, pp 290–294, Feb. 1970.*

Meyer et al. "Mapping of deletions in the genome of the highly attenuated vaccinia virus MVA and their influence on virulence." Journal of General Virology. vol. 72, pp 1031–1038, 1991.*

Mayr et al. "Radioprotective effectiveness of the paraimmunity inducer "PIND–AVI" : investigation using the model "protective tetanic vaccination in mice" after exposure to X–ray." Strahlentherapie. vol. 156, No. 11, pp 795–799, Nov. 1980.*

* cited by examiner

Primary Examiner—Donna C. Wortman
(74) Attorney, Agent, or Firm—Alice O. Martin; Barnes & Thornburg

(57) ABSTRACT

Multipotent paramunity inducers are described which are based on combinations of poxvirus components derived from various poxviruses with paramunizing properties and which have been improved in terms of their potency and their paramunization-related activities as compared with the known paramunity inducers. The invention also relates to a method for preparing these multipotent paramunity inducers and to their use as drugs.

8 Claims, 2 Drawing Sheets

PARAMUNITY INDUCER BASED ON COMBINATIONS OF POXVIRUS COMPONENTS, PROCESS TO PREPARE IT AND ITS USE AS MEDICAMENT

This invention relates to multipotent paramunity inducers based on combinations of poxvirus components, a method for preparing same, and their use as drugs.

The immune system of warm-blooded animals, especially of mammals and birds, consists of an antigen-specific part and an antigen non-specific part. The two parts are cross-linked and so form a uniform organic system. The antigen-specific mechanisms are responsible for building up an immunity, while the antigen non-specific are responsible for building up paramunity. Accordingly, for both historical and functional reasons the antigen non-specific part of the defence is known as the paraspecific immune system. Up until the present, immunology research has been mainly concerned with the antigen-specific part of the immune system, i.e. with how immunity is formed. The utilization of this defence potential led for example to the development of active and passive immunization. In contrast, the exploitation of the paraspecific activities of the immune system for prevention and cure is still in its early stages. The paraspecific immune system makes it possible for the organism to mount an immediate defence when confronted by the most diverse foreign substances, infectious pathogens, toxins and transformed cells of the organism itself. There are patterns of close functional interplay between the paraspecific and the specific activities of the immune system, generally involving a flow of information from the paraspecific mechanisms, which react first, to the specific mechanisms of the immune system. In this way, in cases where there is infection with particularly virulent pathogens the paraspecific defence of the organism is able to bridge the gap until specific immunity has had time to develop.

Since Edward Jenner introduced protective immunization against smallpox in 1798 using a vaccine obtained from animals (cattle or horses) and based on the vaccinia virus, empirically obtained results have been reported showing that protective immunization against smallpox resulted in those vaccinated recovering surprisingly rapidly, or without complications, from other infections and diseases, especially chronic and relapsing complaints, from which they happened to be suffering at the time of vaccination. In particular this applies to herpes infections of varying genesis, papillomas, chronic eczemas and pathological conditions of the ears, nose and throat. As well as this, however, it was noted that those immunized showed a generally raised short-term level of resistance to acute ambient infections. Similar phenomena have been noted after protective immunization against forms of animal pox. It was deduced from these findings that poxviruses or certain structural components of these viruses can positively influence the organism's ability to resist infections and tumours, on a non-specific level. Because these non-specific healing processes commence immediately after vaccination and hence 5 to 7 days before the specific immunity conferred by vaccination develops, as well as parallel thereto, in 1978 A. Mayr designated these non-specific consequences of a prophylactic immunization as "paraspecific". Accordingly, medicaments produced specifically to exploit such paraspecific effects are known as "paramunity inducers"; see A. Mayr, 'Prämunität, Prämunisierung und paraspezifische Wirkung von Schutzimpfungen', Münch. Med. Wschr. 1978, Vol. 120, pp. 239 to 242; A. Mayr, H. Raettig, H. Stickl and M. Alexander, 1979: 'Paramunität, Paramunisierung, Paramunitätsinducer', Fortschr. Med. 97, pp. 1159 to 1165 and 1205 to 1210.

DE-A-27 14 665 and U.S. Pat. No. 4,191,745 disclose preparations based on poxviruses for treating herpes zoster and other herpes infections. In veterinary medicine, paramunity inducers have been produced from purified, attenuated and inactivated avipox and parapox viruses. These paramunity inducers are registered in the European countries as "Duphapind$^R$" and "Duphamun$^R$" (PIND-AVI) and as "Baypamun$^R$" (PIND-ORF) for virtually all species of farm and domestic animals. Paramunity inducer PIND-AVI is prepared from an attenuated avipox virus, strain HP-1, and paramunity inducer PIND-ORF is prepared from an attenuated parapox virus, strain D-1701. The attenuated viruses are rendered inactive in a manner known per se, e.g. by γ-radiation or chemical means such as treatment with β-propiolactone.

The drugs with paramunizing properties which are preferred for use as immunostimulants and to provide "adjuvant immunotherapy" in human medicine are BCG (Bacillus Calmette Guerin), levamisole and Corynebacterium parvum (syn. Propionibacterium acnes). However, these preparations are inferior to the poxvirus-based paramunity inducers in terms of their paramunizing action, as may be seen from the results summarized in Table 1, which were obtained in tests in which these preparations were compared with PIND-AVI and PIND-ORF in the VSV baby mouse test; see A. Mayr, A. M. Büttner, S. Pawlas, V. Erfle, B. Mayr, R. Brunner and K. Osterkorn, 1986: 'Vergleichende Untersuchungen über die immunstimulierende (paramunisierende) Wirksamkeit von BCG, Levamisol, Corynebacterium parvum und Präparaten aus Pockenviren in verschiedenen "in vivo"—und "in vitro"—Testen', J. Vet. Med. B 33, pp. 321 to 339.

It is the object of the present invention to provide, for therapeutic applications in human and veterinary medicine, multipotent paramunity inducers based on poxvirus components, which have been improved in respect of their potency and in respect of their paramunization-related activities. It is a further object of the present invention to provide an improved method for preparing said multipotent paramunity inducers using a new technique of virus propagation in cell cultures and/or virus inactivation. Lastly, it is yet another object of the invention to provide pharmaceutical compositions for use as drugs based on said multipotent paramunity inducers.

The invention therefore relates to multipotent paramunity inducers based on a combination of two or more poxvirus components derived from various poxvirus strains having paramunizing properties. The invention further relates to multipotent paramunity inducers based on a combination of a plurality of different species of inactivated, attenuated poxviruses with paramunizing properties. The invention also relates to a method for preparing paramunity inducers in which two or more poxvirus components derived from different poxvirus strains with paramunizing properties are combined. Lastly, the invention relates to methods for preparing the multipotent paramunity inducers according to the invention, and to pharmaceutical compositions comprising said multipotent paramunity inducers, for use as drugs.

It was unexpectedly found that combining poxvirus components in the multipotent paramunity inducers according to the invention does not result in a decrease in, let alone loss of, the respective paramunizing activities of the individual poxvirus components. Instead it was seen that combining the poxvirus components derived from various poxvirus strains in the multipotent paramunity inducers according to the invention brings about not only an additive or supplementary effect, but a potentiation of the respective paramunizing action. Experiments have shown that the action of the multipotent paramunity inducers combined from poxvirus components far exceeds their respective individual actions. This phenomenon could not have been predicted, and in terms of their potency and their paramunisation-related activities it enhances these paramunity inducers as compared with conventional preparations from a single poxvirus component. Another unexpected finding is that the multipotent paramunity inducers according to the invention have virtually no immunogenic properties, but do have very strong paramunizing properties, as a result of which they can safely be administered on a repeated or continuous basis.

The invention is also based on the unexpected finding that a competitive situation exists between the epitopes of the structural proteins of the poxviruses responsible for paramunization and those responsible for immunization. The steeper the decline in activity on the part of the epitopes responsible for antigen-specific immunization, the greater is the increase in paraspecific activity. This is attested by the following two observations:

a) Attenuation over several hundred passages in cell cultures causes the immunizing properties of poxviruses to decrease, whilst the paraspecific activities not only increase but in the case of certain pox strains only appear after attenuation;

b) inactivation of the poxviruses suited to preparation of the paramunity inducers, preferably by irradiation, heat or pH action, or most preferably by chemical treatment with β-propiolactone under specific conditions, causes the poxviruses to lose their immunizing properties whereas their paramunizing activities increase.

The inventive combinations of the poxvirus components are suited for use as multipotent paramunity inducers in both human and veterinary medicine.

The term "poxvirus component", as employed in the context of this invention, covers a large number of viral structures derived from poxviruses with paramunizing properties, for example viable (i.e. capable of multiplication) or inactivated freshly isolated poxviruses, viable or inactivated recombined poxviruses derived from freshly isolated poxviruses, viable or inactivated attenuated poxviruses, viable or inactivated recombined poxviruses derived from attenuated poxviruses, the detached envelopes and cleavage products and aberrant forms of said envelopes of the poxviruses listed above, individual viral polypeptides obtained by biochemical or immunochemical methods from cultures that had been infected with the poxviruses listed above, and recombinant viral polypeptides obtained by means of prokaryotic or eukaryotic expression and at least parts of which are derived from one or more of the viral polypeptides of the poxviruses listed above.

The term "combination", as employed in the context of this invention, covers both the mixing of two or more individual poxvirus components derived from different strains of poxvirus, and also the fact of combining a plurality of such individual poxvirus components in a polypeptide or polypeptide complex. Components derived from poxviruses, for example recombined poxviruses, individual viral polypeptides or recombinant viral polypeptides, which as a result of mutation or genetic manipulation comprise two or more polypeptide sequences derived from two or more poxvirus strains, will consequently be dealt with as though they were two or more discrete poxvirus components, irrespective of the fact that said polypeptide sequences constitute parts of a single amino acid chain. The same also goes for individual poxvirus components that are interconnected physically or chemically in any way.

The term "multipotent", as employed in the context of this invention, denotes the many and diverse potential applications of the paramunity inducers under the invention as regards prophylaxis and therapy, e.g. for the following indications:

1) infectious factor diseases and mixed infections, chronic manifestations of infectious processes, persistently relapsing infections, and bacterial and viral infections that are resistant to chemotherapy, 2) weaknesses in, or irregularities of the immune system of an organism, 3) the threat of neonatal infections, 4) adjuvant therapy in certain forms of cancer and/or prevention of metastasization, 5) regulation of homeostasis between the hormonal, circulatory, metabolic and nervous systems.

The paramunity inducers are particularly suitable for prophylactic use in the following instances:

Rapid activation of neonate immunity

Before expected stress situations (house-moving, mental stress, high-performance periods, etc.)

Before hospitalization

When there is acute danger of infection

Prevention of vaccination complications

Reducing the danger of tumours and/or metastasization

In support of bioregulation

Raising performance levels

Raising life expectancy

Regulation of homeostasis in interplay with the hormonal, circulatory, metabolic and nervous systems.

The paramunity inducers are particularly suitable for therapeutic use in the following instances:

Immune weaknesses

Virus diseases, therapy-resistant bacterial diseases, infectious factor diseases Chronic and relapsing infections Tumours Convalescence Chemotherapy and antibiotic treatment Liver diseases of differing etiology Chronic skin diseases Immunopathogenic secondary diseases.

Table 1 shows the paramunizing effects of various poxvirus components and paramunity inducers in the VSV baby mouse test. The figures shown represent the efficacy indices. The procedure employed is outlined in DE-A-27 14 665.

Table 2 shows the potentiation of the paramunizing efficacy of various poxvirus strains in the VSV test as a function of the degree of attenuation involved. Inactivated virus suspensions were used.

Table 3 shows what effect attenuation has on the induction of interferon synthesis of mononuclear leucocytes of peripheral blood in various species.

Table 4 shows how the paramunizing effect of a multipotent paramunity inducer based on a recombinant poxvirus intensifies as compared with the effect of individual components.

For use as poxvirus components for the multipotent paramunity inducers according to the invention, poxvirus species may be used as freshly isolated, so-called virulent field strains, or else in attenuated, avirulent form. Because the paramunizing properties increase in the course of attenuation as compared with non-attenuated strains, and also on account of safety considerations, the use of attenuated strains is preferred. This involves propagating the relevant virus strains in serial passages in cell cultures. By regularly interpolating clonal selection using plaque technology, genetically uniform virus material is obtained which has adapted itself particularly well to the culture conditions thanks to mutation and selection. The degree of attenuation is verified in the course of the passages by inoculation onto receptive hosts (e.g. using the cutan method in the case of chicks, canaries, etc., scarification of rabbit skin, etc.). The various identification methods belong to the prior art; see A. Mayr and E. Munz, 1964: 'Veränderungen von Vaccinevirus durch Dauerpassagen in Hühnerembryofibroblasten-Kulturen', Zbl. Bakt. Hyg. I. Orig. 195, pp. 24 to 35; A. Mayr, F. Hartig and I. Bayr, 1964: 'Entwicklung eines Impfstoffes gegen die Kanarienpocken auf der Basis eines attenuierten Kanarienpocken-Kulturvirus', Zbl. Vet. Med. B 12, pp. 41 to 49; A. Mayr and K. Malicki, 1966: 'Attenuierung von virulentem Hühnerpockenvirus in Zellkulturen und Eigenschaften des attenuierten Virus', Zbl. Vet. Med. B 13, pp. 1 to 13; A. Mayr, M. Herlyn, H. Mahnel, A. Danco, A. Zach und H. Bostedt, 1981: 'Bekämpfung des Ecthyma contagiosum (Pustulardermatitis) der Schafe mit einem neuen Parenteral-Zellkultur-Lebendimpstoff', Zbl. Vet. Med. B 28, pp. 535 to 552. It is standard practice to use several different methods for determining the degree of attenuation of the poxvirus species concerned.

The serial passages used for attenuation usually conclude with triple clonal selection using plaque final dilution technology. This ensures that the virus material being used is genetically uniform. All the poxvirus strains cited hereinafter were obtained according to this principle.

Attenuation of avipox virus requires 200 to 500 culture passages, preferably at least 440 passages. Attenuation of parapox virus takes 100 to 200 culture passages, preferably at least 170 graduated passages, initially in embryonal lamb kidney cultures and followed by passages in embryonal calf lung cultures and in cell lines of monkey kidneys (e.g. MA, Vero). The MVA vaccinia virus requires attenuation over 400 to 600 culture passages, preferably at least 575 passages. Attenuation of canarypox virus takes from 200 to 500 culture passages, preferably at least 390 passages. It takes from three to five years to perform each 100 passages, depending on the species of poxvirus concerned. Attenuation thus encompasses a period lasting from ten to twenty years.

Attenuated poxviruses preferably used as the poxvirus component for the paramunity inducers of the invention are the avipox virus, strain HP-1, 444th passage in CEF cultures, the parapox virus, strain ORF D1701, 135th passage in embryonal lamb kidney cultures, 37th passage in bovine embryonal lung cell cultures (BEL), 49th passage in MA cells (monkey kidney cell line), the vaccinia virus, strain MVA (modified vacciniavirus Ankara), 572nd passage in CEF cultures, and the canarypox virus, strain KP-1, 535th passage in CEF cultures. Samples of these viruses are on deposit in the form of lyophilisates at the European Collection of Animal Cell Cultures (ECACC), PHLS Centre for Applied Microbiology and Research, Porton Down, Salisbury, Wiltshire, SP4 0JG, England. The respective serial numbers of the deposits are V94012709, V94012706, V94012707 and V94012708; see also the indications to deposited microorganisms on the following pages. Further indications relating to the deposited viruses can be taken from the subsequently following copies of the accession forms for virus deposits.

Alternatively, however, it is possible to use other attenuated poxvirus strains with paramunizing properties to prepare the multipotent paramunity inducers according to the invention.

Various methods are suitable for preparing the recombinant poxviruses within the meaning of the invention. A preferred method involves simultaneous infection using two different poxvirus strains with paramunizing properties to provoke recombination phenomena in which parts of the areas coding for the paramunizing properties of one virus are introduced into the genome of a different poxvirus. Next, recombined poxviruses which unite the paramunizing activities of two different poxvirus strains are identified using plaque final dilution passages and appropriate screening processes. Various combinations of avipox virus, vaccinia MVA virus, canarypox virus or parapox virus are for example suitable for simultaneous infection.

Another method of preparing recombined viruses additionally makes use of genetic engineering techniques and the procedure of homologous recombination. For this it is first necessary to identify the areas coding for the paramunizing properties of the poxviruses. This is done by means of techniques known per se.

For example, the paramunizing structural proteins can be fractionated using biochemical or immunochemical methods and their paramunizing properties investigated. This may for instance be done using the in vitro and in vivo tests cited below. Once the paramunizing structural proteins have been identified, N-terminal sequences of the entire protein or of its proteolytic or chemical cleavage products can then be sequenced to obtain amino-acid sequence information that permits screening for the corresponding DNA sections in appropriate gene banks using suitably designed oligonucleotide probes, using either traditional hybridization techniques or the polymerase chain reaction (PCR). Another possible method of identification is by hybridization under conditions of decreased stringency using known DNA samples of a poxvirus species that are specific to proteins with paramunizing properties, and isolating the corresponding homologous DNA sections of other poxviruses that likewise code for proteins with paramunizing effect. In this process, too, it is possible to replace the conventional method of screening by the PCR with corresponding primers that are homologous with the known sequences.

DNA sections of other poxviruses that are homologous with known DNA sections of certain poxviruses and that code for paramunizing proteins can also be identified by means of restriction enzyme mapping of the genome of various related poxviruses and comparison of the areas with similar restriction enzyme cleavage patterns. This type of comparative restriction enzyme mapping is for example described in F. Rafii and D. Burger: 'Comparison of contagious Ecthyma virus genomes by restriction endonucleases', Arch. Virol. 84, pp. 283 to 289, (1985).

A further way to identify DNA sections coding for paramunizing properties is to use monoclonal or polyclonal antibodies that recognize viral proteins with paramunizing properties to screen gene banks. Such a method has, for example, been used to identify the rabbit poxvirus gene that codes for the 14 kD protein (fusion protein) with paramunizing properties occurring in poxviruses.

Following identification and cloning of the DNA sections that code for paramunizing viral proteins, it is then possible to specifically prepare the recombined poxviruses according to the invention by means of homologous recombination using suitable vectors. A suitable insertion site for the foreign DNA would, for example, be the locus for the thymidine kinase gene, as it is not essential for poxviruses. The method involves the transfection of a transfer vector carrying the heterologous gene section that is to be introduced into the poxvirus via homologous recombination and that has been derived from another poxvirus with paramunizing properties, into cells that have been infected with the poxvirus that is to be recombined. Preferably the transfer vectors will carry a selection marker gene, as well as homologous, flanking sequences derived from the poxvirus to be recombined, in order to make homologous recombination phenomena possible at a satisfactory rate. This is then followed by identification of recombined poxviruses that combine the paramunizing activities of two different poxvirus strains, once again using plaque final dilution passages and suitable screening processes such as immunochemical individual plaque detection by means of monoclonal or polyclonal antibodies. The inserted DNA constructs can also be detected using hybridization techniques, e.g. by means of "dot blot" hybridization. Expression of the insert is either detected directly by the detection of the relevant structural protein with monoclonal or polyclonal antibodies, or else indirectly via the immune-paramune response of laboratory animals (VSV challenge test), in cell cultures (cell culture challenge test) or by in vitro parameters (interferon induction, formation of certain interleukins, CSF, TNF, etc.). The result is a recombinant poxvirus that can be used as a poxvirus component or as a multipotent paramunity inducer within the meaning of the invention.

Attenuated poxviruses are especially suitable for the preparation of the recombined poxviruses according to the invention, for they are known not only to be environmentally safe but at the same time to possess very good paramunizing efficacy.

The attenuated recombined poxviruses can also be used both in viable form and in inactivated form to produce the multipotent paramunity inducers and pharmaceutical compositions of the invention. Use of the inactivated recombined poxviruses is preferred.

Examples of viable or inactivated recombined attenuated poxviruses with paramunizing effect that are suitable for use as poxvirus components are the MVA virus carrying avipoxvirus and parapoxvirus genes that code for paramunizing proteins, attenuated canarypox virus carrying MVA virus, avipox and parapox virus genes that code for paramunizing proteins, and "vice versa" combinations of the most diverse, attenuated poxvirus strains.

Propagation of the aforementioned poxviruses used as poxvirus components for the multipotent paramunity inducers of the invention may take place in both primary and secondary cell cultures, as well as in permanent cell lines. Propagation and cultivation of the poxviruses used in accordance with the invention is by per se known techniques. For example, attenuated avipox virus can be propagated in primary or secondary fibroblasts from chicken embryos (CEF cultures) and cultures of permanent CEF cells (chicken embryo fibroblasts; cell line). Propagation in primary CEF cultures is preferred. Attenuated parapox virus may, for example, be propagated in lamb kidney cultures or bovine embryo lung (BEL) cultures (primary or secondary cultures; for instance prepared by the method of S. H. Madin, P. C. Andriese, N. B. Darby, 1957: 'The in vitro cultivation of tissues of domestic and laboratory animals', Am. J. Vet. Res. 18, pp. 932 to 941), vero and MA cells (kidney cell lines of the African green long-tailed monkey; ATCC CCL 81 and Microbiology Associated 104). Propagation in vero cells is preferred. The MVA vaccinia virus can for example be propagated in primary CEF cultures or CEF cell strains (cell line). Propagation in CEF cultures is preferred. Canarypox virus can be propagated in CEF cultures and in permanent CEF cells. Propagation in primary CEF cultures is preferred.

In the case of attenuated avipox virus, MVA vaccinia virus and attenuated canarypox virus, propagation is preferably in primary or secondary cell cultures of mammals or birds that are receptive to said viruses. In primary or secondary CEF cultures propagation preferably takes place at 33° C. to 39° C., most preferably at 37° C. CEF cell cultures are prepared by the conventional method of trypsinization of the trunk and limbs of the chicken embryos incubated for 10 to 12 days, after removal of the entrails and head (fibroblast culturing), in corresponding glass or plastic containers suitable for cell cultures, e.g. penicillin bottles, using stationary incubation or rotary incubation (roller cultures). Most preferred of all is to modify the standard technique and use the entire embryo, including the head and entrails (mixed cell suspension, better virus harvests with more stable quality and quantity of the paramunizing properties). The primary cultures are preferably obtained by a pretrypsinization (10–15 minutes, removing of the supernatant) and a main trypsinization over 45–60 minutes. The medium for taking into culture preferably consists of minimal essential medium +10% lactalbumin hydrolyzate +10% BMS (serum substitute); the medium for maintenance consists solely of MEM. The cell cultures are infected with virus shortly before "densification" (80 to 100% confluent cell sheet), i.e. 1 to 3 days after plating, preferably 20 hours after plating, and incubated at 33° C. to 39° C., most preferably at 37° C.

The preferred virus for inoculation onto CEF cultures is plaque-purified virus material of the relevant attenuated poxvirus strain. The preferred inoculating dose is $10^{7.0}$ $TCID_{50}$/100 ml medium ($TCID_{50}$=50% tissue culture infectious dose).

The infected cell cultures are incubated at 33° C. to 39° C., preferably 37° C., in order to obtain suspensions of the attenuated poxviruses from cell cultures for use for the multipotent paramunity inducers. The viral material is harvested after 1 to 10 days, preferably after 3 to 4 days, and preferably when 5 to 100% of the cell sheet have been destroyed, most preferably with a 5 to 60% status of spherical, rounded cells and 40 to 95% lysis. A sufficient quantity of the virus suspension is removed in order to carry out the usual bacteriological, virological and mycological checks under the international regulations on the control of contaminations. Next the cells are stored in their entirety at +4° C., −20° C. to −80° C. or lower temperatures, preferably at −80° C. The cultures remain at this temperature until the bacteriological, virological and mycological checks have been completed. If all the checks satisfy the safety regulations the virus harvests are thawed out. This destroys cells that are still intact and thus releases cell-bound virus, thereby enabling the virus titer to increase. The cells are preferably broken down by repeated freezing and thawing, most preferably by treatment with ultrasound. This is followed by another check on sterility and a check on the infectiosity titer.

The procedure used to cultivate and propagate the attenuated parapox virus is the same as that already described in respect of the attenuated avipox virus, vaccinia virus and canarypox virus. The only difference lies in the use of primary or secondary lamb kidney cultures, bovine embryo lung cell cultures or various cell lines such as vero cells or MA cells (in both cases cell strains taken from embryo monkey kidneys) as cell cultures. Vero cells are preferred for the preparation of parapox virus suspensions.

It is also possible to prepare the multipotent paramunity inducers according to the invention using the detached envelopes of unrecombined or recombined poxviruses as poxvirus components, as well as aberrant forms of said envelopes resulting from incomplete synthesis of virus particles.

Virus envelopes are preferably prepared by splitting the virus envelope away from the virus core (nucleocapside), in such a way that suspensions of poxviruses obtained in the foregoing manner are incubated with a detergent under reducing conditions and the virus particles so split are separated into virus cores and virus envelopes by means of density gradient centrifugation.

Another preferred method of recovering paramunizing virus envelopes of poxviruses or aberrant forms of these envelopes is to infect cell cultures that are not permissive for the various poxvirus species. One example of such a constellation is the culturing of attenuated ORF virus in chicken embryo fibroblasts. The respective poxvirus species go through an abortive proliferation cycle in the non-permissive cell cultures. In other words, there is no assembly of finished, infectious virus particles in the viroplasma zones of the infected cells. The synthesized, abortive precursors of the virus ("empty envelopes", incomplete forms, aberrant forms, etc.) already contain the structural proteins responsible for paramunization. They are secreted into the culture medium or may be released by lysis of the infected cells. They are isolated, purified and concentrated by the methods outlined above.

It is preferable to use the foregoing poxviruses in attenuated form to prepare the foregoing virus envelopes and aberrant forms of virus envelopes. One preferred method for preparing virus envelopes is described below in Example 6.

It is also possible to use viral polypeptides as the poxvirus component within the meaning of the invention. Such viral polypeptides are normally viral structural proteins with paramunizing properties, which can be prepared by various methods, usually by purification from cell cultures that have been infected with poxviruses. These cell cultures are preferably the ones described above, and it is possible to use both those in which the host cells are permissive in respect of the infecting poxviruses and those that are not permissive in respect of the poxviruses. The viral polypeptides are purified using conventional biochemical or immunochemical methods, for instance by the use of monoclonal antibodies for immune affinity chromatography. Preferred proteins purified by these processes for example include structural protein fractions of poxviruses with a molecular weight of 14 KDa (fusion protein) or 30 KDa (adsorption protein). The fusion protein stimulates phagocytosis, interferon synthesis and the formation of interleukins. The adsorption protein, which is common to all orthopox species, stimulates the NK cells, granulocytes and macrophages and uses effector cells to bring about the formation of interferons and certain interleukins.

Paramunizing viral polypeptides may also be recovered directly by cleavage of the poxvirus particles, followed by isolation, fractionation (e.g. by molecular weight), purification and concentration (e.g. using density gradients, ultracentrifugation, chromatography, preparative SDS polyacrylamide gel electrophoresis or other conventional processes). Example 8 sets out a method for purifying viral polypeptides obtained from preparative SDS polyacrylamide gels.

Following the identification of gene sections coding for proteins with paramunizing properties, already mentioned in connection with the preparation of recombined viruses, the DNA sections cloned and characterized in this manner can also be used to prepare recombinant viral polypeptides. Suitable expression systems for their preparation include prokaryotic or eukaryotic expression vectors based on plasmids, phages or viruses, for example those suited to expression in *E. coli,* yeast or mammalian cells. Those suited to expression in mammalian cells are particularly suitable.

Conventional genetic engineering methods (A. Mayr: 'Virologische Arbeitsmethoden', vol. 3, published in 1989 by Fischer Verlag, Jena) are employed to transfer the DNA sections by the known methods into the phage or plasmid vectors or into vectors based on viruses and to express them in the appropriate host cells. The expressed proteins are then purified by conventional methods and constitute the starting material for corresponding combinations of poxvirus components. Recombinant expression not only enables a DNA section coding for a viral polypeptide with paramunizing properties to be expressed, but such DNA sections can also be cloned into the expression vector in a way that leads to expression of the resulting viral polypeptide as a fusion protein. A number of polypeptide sequences would make suitable fusion protein components for fusion with the viral polypeptide portions, e.g. sequences derived from bacterial β-galactosidase (lacZ); the DNA sections that code for these components are usually already present in the vector systems used for expression. However, the fusion proteins suitable as poxvirus components within the meaning of the present invention may also be fusions of two or more different viral polypeptides derived from different paramunizing poxvirus strains. These last-named fusion proteins unite paramunizing polypeptide areas of different poxviruses in one polypeptide and are obtained by combining together two or more of the DNA sections coding for said polypeptide areas in an appropriate order and in the correct reading frame.

It may be necessary to employ further purification methods in order to use the poxvirus components as multipotent paramunity inducers for human medicine. For example the preparation can be additionally purified using further purification methods known per se, including ultracentrifugation, density gradient centrifugation, etc.

The poxvirus strains or recombinant virus strains can be inactivated with various treatment procedures, e.g. heat treatment, using physical or chemical means or by pH action. Inactivation is preferably by gamma radiation or treatment with β-propiolactone, and the treatments concerned must be performed in conditions that do not destroy the paramunizing properties.

The most preferred embodiment involves inactivating the attenuated poxvirus with β-propiolactone in a pH range of between 8 and 9. The treatment with β-propiolactone is preferably carried out under the following conditions: The pH of the virus suspension is adjusted to 8.6 using $NaHCO_3$ (8.8% in distilled water). β-propiolactone is initially diluted 1:10 with distilled water and, taking suitable precautions, is added to the virus suspension in a ratio of 0.5 to 100. This corresponds to a 0.05% dilution of β-propiolactone. This suspension is stirred for 1 hour at refrigerator temperature (+4 to +8° C.) and for 4 hours at 37° C. and then stored in a refrigerator for approx. 12 to 18 hours (overnight). The inactivated suspension is purified by centrifugation for 10 minutes at 2600 rpm. The pH is then checked again and readjusted if necessary.

Proof of inactivation is by inoculating CEF cultures with test samples of sufficient volume of the treated material. If no typical cytopathic changes have developed no later than nine days after the inoculation, this is taken to be an indication that inactivation is complete. Should there be any suspicion of non-inactivated residual virus, three sub-passages are carried out. In addition another check is made for contamination with viruses, bacteria or fungi in suitable cultures or on suitable culture media, as well as by investigation using an electron microscope.

The solutions or suspensions of the poxvirus components are preferably lyophilized following purification. Suitable stabilizers are preferably added to the poxvirus components prior to lyophilization. In cases involving suspensions of attenuated poxviruses, a stabilizer such as Kollidon$^R$, Molico$^R$ (low-fat milk powder) or gelatin is added to the poxvirus suspension. The most preferred embodiment involves adding succinylated gelatin (manufactured by Hausmann of St. Gallen, Switzerland) in a final concentration of 2.5%. Before the gelatin is added (50% concentration) its pH must be adjusted to 8.0. This also applies to other stabilizers.

The finished preparation is divided into portions, e.g. into 2 ml quantities, and lyophilized. The lyophilized multipotent paramunity inducer will remain stable for at least 10 years when stored at temperatures between +4° C. and +8° C. or below. The units of efficacy of the lyophilizate determined by the VSV challenge test or cell culture challenge test do not change over a period of at least 10 years under these conditions (the term "unit of efficacy" is defined below). Prior to being put into final storage, the purity of the lyophilizate is again checked bacteriologically, virologically and toxicologically.

The poxvirus components produced in the manner described above for the preparation of the paramunity inducers according to the invention are combined with one another in various mixing ratios in order to potentiate their efficacy. In the case of attenuated poxviruses the mixing ratio is preferably 1:1. Combinations are also possible in, for example, the following mixing ratios:

1. avipox virus and parapox virus 5:1 to 1:5, preferably 2:1 to 1:2,
2. avipox virus, parapox virus and MVA vaccinia virus 6:3:1 to 1:3:6, preferably 6:3:1, most preferably 1:1:1,
3. avipox virus, parapox virus, MVA and canarypox virus inducers in a ratio of 1:1:1:1.

Corresponding mixing ratios may also be used for the other poxvirus components according to the invention. However, other mixing ratios are likewise suitable for the preparation of the multipotent paramunity inducers of the invention.

Combination of the poxvirus components for preparing the multipotent paramunity inducers of the invention can take place at various points of the process for their preparation, preferably before they are treated to inactivate them, before lyophilization or after lyophilization. If poxviruses are used as the poxvirus components it is preferable to combine the components before they undergo inactivating treatment.

The efficacy both of the multipotent paramunity inducers according to the invention and the individual poxvirus components can be demonstrated by various methods: The VSV infection model in the baby mouse is used as in vivo proof; see Mayr et al. (1986), ibid. This model may be used at the same time for assaying the units of efficacy (UE/ml). Table 1 represents the efficacy of various dilutions of PIND-AVI and PIND-ORF in the VSV model. The efficacy index of a preparation, or of a dilution stage, is calculated by the following formula:

$$\text{Efficacy index}(EI) = \frac{b-a}{b} \times 100$$

a=% mortality of the test group
b=% mortality of the control group

The dilution stage at which an efficacy index of at least 20 is still achieved contains 1 UE per 0.1 ml (infection dose per baby mouse), or 10 UE/ml. In the example with PIND-AVI the final titer is 1:16; accordingly the batch contains 160 UE/ml).

Various test methods can be used as in vitro proof for the efficacy both of the multipotent paramunity inducers according to the invention and of the individual poxvirus components:

a) the activity of peritoneal NK cells 24 hours after treatment with PIND-AVI in the 4-hour chromium-51 release test; Mayr et al. 1986, ibid.,
b) colony-stimulating activity in the serum of mice 8 hours after treatment; see G. Wolf, 1986: 'Koloniestimulierende Aktivität in Mäuseseren nach Vorbehandlung mit Inducern aus Pockenviren und anderen Mikroorganismen'; Czerny 1990, ibid., and
c) interferon synthesis in mononuclear leucocytes in peripheral blood; see M. Steinmassl and G. Wolf, 1990: 'Bildung von Interleukin-2 und Interferon$_a$ durch mononukleäre Leukozyten des Schweines nach in vitro-Stimulation mit verschiedenen Viruspräparaten', J. Vet. Med. B 37, pp. 321 to 331. However, alternative methods of detection may also be used, for instance measurement of the activity of the tumour necrosis factor (TNF) in pretreated rabbits or mice in the L929 cytotoxicity test, the challenge test in the adult mouse with the Aujeszky virus, the determination of colony-stimulating activity (CSA) in the serum of various animals and the measurement of granulocyte activity in humans and animals in the "FACS analyzer" (particle uptake, "respiratory burst").

The multipotent paramunity inducers obtained by the foregoing methods may be used as the starting product for the preparation of pharmaceutical compositions for use as drugs. To this end, standard pharmaceutical vehicles may be added to the lyophilizate according to the starting volume, preferably sterile, pyrogen-free distilled water. In this formulation it is suitable for both parenteral (e.g. intramuscular or subcutaneous) and local administration. The multipotent paramunity inducers according to the invention are non-toxic, pyrogen-free and for instance do not cause abnormal postvaccinal reactions when injected intramuscularly.

The pharmaceutical compositions according to the invention also encompass other formulations. Examples of formulations for local application include sucking tablets, ointments, suppositories, nose drops, nasal sprays, etc. Examples of formulations for parenteral application include injection preparations. They are produced by processes known per se.

Further examples of suitable formulations of the pharmaceutical compositions within the meaning of the invention include rectal or vaginal suppositories. In either form they can be used to treat haemorrhoids and vaginal inflammation or other vaginal lesions. Care must be taken in their manufacture to ensure that constituents of the carrier, for instance those having proteolytic activity, do not adversely affect sterility and stability.

For prophylactic use the multipotent paramunity inducers are preferably administered 1 to 3 times at 24 hour intervals. For therapeutic use it is preferable, depending on the severity of the particular condition, to carry out 1 to 3 treatments daily for a period of 3 to 5 days, or until the clinical symptoms subside. The dose depends on the symptoms being treated and on the form of administration chosen. In parenteral application the standard dose usually is 2 ml, with one dose preferably containing at least 160 units of efficacy. However, it is possible to vary the dose and application method to suit individual circumstances.

The examples which follow are intended to elucidate the invention further.

EXAMPLE 1

The starting material used to prepare a poxvirus component according to the invention was the avipox strain HP1, which had been isolated from a generalized diseased chicken and attenuated in 440 culture passages in chicken embryo fibroblast (CEF) cultures. Clonal selection using the plaque final dilution technique and control tests for immunogenity and paramunizing efficacy were performed at regular intervals in the course of the attenuation passages. The 440th CEF passage served for preparation of the poxvirus component of the invention, having again undergone clonal selection by the plaque technique in the final three passages to enable us to work with genetically uniform material. Table 2 highlights the differences between virus material from early and later cell culture passages in relation to paramunizing efficacy.

CEF cultures were prepared by a modified method based on the standard technique involving culturing the chick embryo in its entirety (including the head and entrails); see A. Mayr, P. A. Bachmann, B. Bibrack and G. Wittmann, 1974: 'Virologische Arbeitsmethoden', vol. 1, published by VEB Gustav Fischer Verlag of Jena. The standard technique was modified by using a totally synthetic medium comprising 10% BMS (serum substitute medium), 10% lactalbumin hydrolyzate and MEM (minimal essential medium). The monolayer cell cultures, with approx. 90% density, were inoculated with the virus strain HP1, 440th passage, infectiosity titer $10^{7.5}$ TCID$_{50}$/ml. An infection dose of $10^7$ TCID$_{50}$/100 ml was used. MEM (without antibiotics) was used as medium for maintenance. The virus was harvested once the cell sheet had been transformed to an extent being 5 to 100% virus-specific. Any remaining cell sheet was loosened by shaking the culture flasks. The viral medium containing cells was treated with ultrasound to allow cells that were still intact to be broken up (for 3 minutes with a 40–50 watt Branson sonifier).

Samples were taken from the virus harvest to check on sterility and infectivity. Only virus harvests that were free from contamination (e.g. by bacteria, viruses, fungi, mycoplasmas) and possessed an infectiosity titer of not less than $10^{7.25}$/ml were processed any further. Virus harvests can be stored at +4 or –80° C. before being further processed.

The pH of the viral material was adjusted to 8.6 prior to commencing inactivation with β-propiolactone. β-propiolactone was added in a concentration of 0.05%. Next the reaction mixture was inactivated by stirring it for 1 hour in the refrigerator, followed by 4 hours in the incubator (at 37° C.). The inactivation process was concluded by storing the virus suspension at rest in the refrigerator overnight. The inactivated virus suspension was purified crudely by centrifugation at 2600 rpm. The inducer thereby recovered was designated PIND-AVI and stored at temperatures of +4° C. or –60° C. and lyophilized once the control checks were complete.

The testing of the resulting attenuated poxvirus suspensions for specificity, purity and harmlessness satisfied the requirements of the European Pharmacopoeia in respect of the following criteria:

1. Electron microscope checking by standard methods revealed typical poxvirus particles in the preparation, some of them empty. The preparation was free from other microbial structures.
2. The standard checks for microbial contamination revealed the preparation to be free from other viruses, bacteria, fungi and mycoplasmas.
3. Toxicity, teratogenity and pyrogenity were tested in accordance with the guidelines of the European Pharmacopoeia, and no positive results were found.
4. Checking for non-inactivated residual viral content: this was done by titration of the finished poxvirus preparation in CEF cultures in the standard manner. In the subsequent 3 passages there was zero residual viral content.

The paramunizing action of the PIND-AVI poxvirus component was demonstrated using the VSV infection model. Table 1 lists the results obtained.

EXAMPLE 2

A poxvirus component according to the invention was prepared from the attenuated MVA vaccinia virus in FCE cultures as in Example 1. As can be seen from Table 2, the paramunizing activity of the virus strain was enhanced by attenuation over at least 500 culture passages. The tests for purity, harmlessness, specificity and efficacy were performed as outlined in Example 1. The same results as in Example 1 were obtained, and these results are summarized in Table 2.

EXAMPLE 3

A poxvirus component obtained from attenuated canarypox virus, strain KP1, was prepared in CEF cultures in the manner outlined in Example 1. As can be seen from Table 2, the paramunizing activity of the virus strain was enhanced by attenuation over not less than 390 culture passages. The tests for purity, harmlessness, specificity and efficacy were performed as outlined under Example 1. The same results were obtained as in Example 1, and these results are exemplified in Table 2.

EXAMPLE 4

A poxvirus component according to the invention was prepared from the attenuated parapox virus, strain D 1701, in MA or vero cells (permanent monkey kidney cell line) in the manner outlined in Example 1. As can be seen from Table 2, the paramunizing activity of the virus strain was enhanced by attenuation over not less than 170 culture passages. The tests for purity, harmlessness, specificity and efficacy were performed as outlined in Example 1. The same results were obtained as in Example 1.

Tables 1 and 2 summarize the results obtained for the individual components (the products of Examples 1 to 4).

EXAMPLE 5

Figure 1:
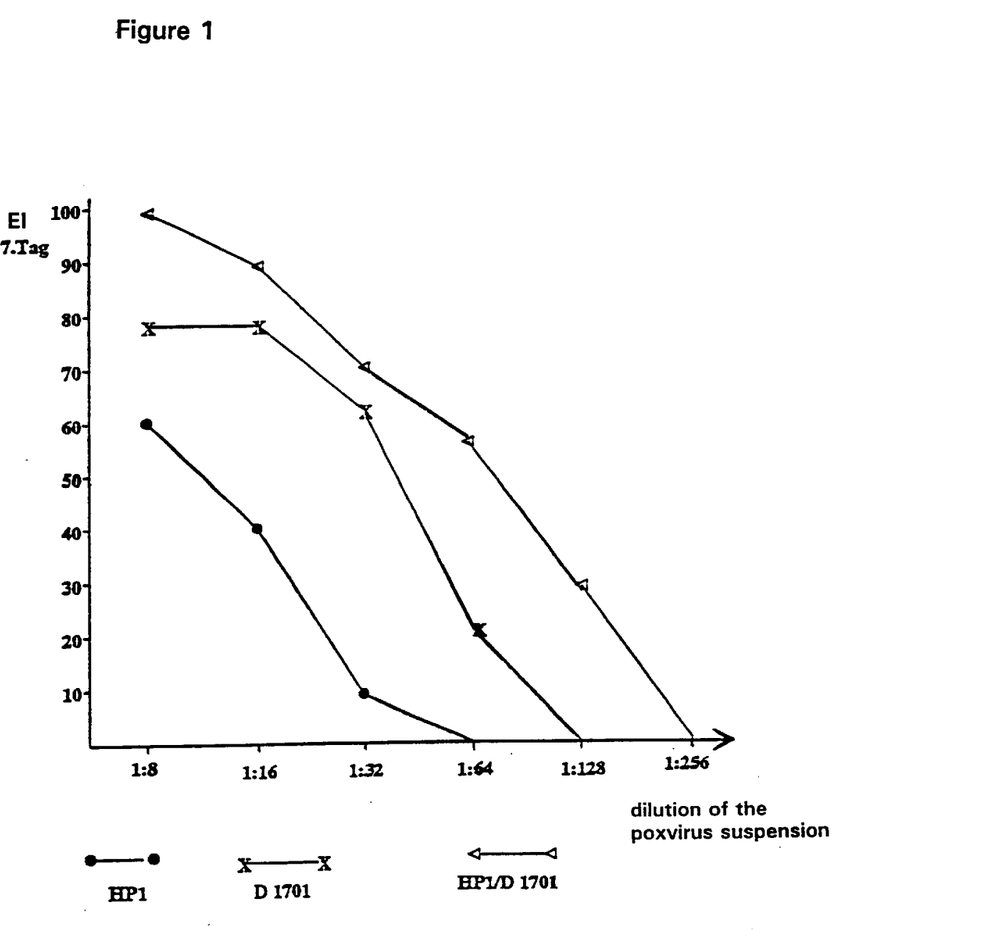
FIG. 1 shows a comparison of the efficacy indices obtained from two VSV tests using attenuated avipox virus HP1, parapox virus ORF D1701 and a combined preparation of HP1 and D1701.

Preparation of a multipotent paramunity inducer within the meaning of the invention was effected in each case by mixing two of the attenuated, inactivated poxvirus suspensions described in Examples 1 to 4 in a 1:1 ratio in a preparation. A mixture of the poxvirus components PIND-AVI and PIND-ORF, as well as of the poxvirus components avipox virus HP1 and parapox virus ORF D 1701, were prepared. As can be seen from Table 1 and FIG. 1, combining the inducers potentiates the paramunizing efficacy. (If the effect were additive, both the efficacy indices of the individual dilutions and their UE/ml would be unchanged.) This is shown clearly by the increase in the two parameters in the depicted instance, respectively by as much as 20–40% (the efficacy index of the combination as compared to 1:8 dilution of D 1701 and HP1, respectively) and by 200–400% (UE/ml of the combination as compared to D 1701 and HP1, respectively). The tests in respect of purity, harmlessness, specificity and efficacy were performed as outlined in Example 1. The same results were obtained as in Example 1, apart from an increased paraspecific activity.

EXAMPLE 6

Vaccinia virus, avipox virus HP1 and parapox virus ORF D 1701 were attenuated as in Example 1 and the effect of attenuation on the paramunizing action was compared in a test which involved measuring the induction of interferon synthesis in mononuclear leucocytes of peripheral blood. Table 3 summarizes the results.

EXAMPLE 7

To prepare a poxvirus component according to the invention, suspensions of MVA vaccina virus and parapox virus ORF D1701 were adjusted to a protein content of 2 mg/ml with PBS and incubated with 1% Nonidet P-40 (NP-40; Sigma) and 50 µl of 2-mercaptoethanol for 60 minutes at 37° C. After underlaying the substratum with 3.5 ml of a 36% sucrose cushion (w/v, in PBS) and centrifugation for 45 minutes in an ultracentrifuge in a Beckmann SW-60 Ti-Rotor at 40,000 rpm (230,000 g) at 4° C., a pellet representing the virus cores was obtained. The detached virus envelopes were in the supernatant. The supernatant was dialyzed extensively against PBS and then used to prepare the multipotent paramunity inducers according to the invention.

EXAMPLE 8

To isolate individual bands of viral protein, 12% SDS polyacrylamide gels were prepared. The buffers and solutions employed were as outlined by U. K. Laemmli (1970), 'Cleavage of structural proteins during the assembly of the head of bacteriophage T4', Nature 227, pp. 680 to 685, and A. Mayr, P. A. Bachmann, B. Bibrack, G. Wittmann, 1989, 'Virologische Arbeitsmethoden, Teil III: Biochemische und biophysikalische Methoden', published by Gustav Fischer Verlag, Jena. Suspensions of MVA vaccinia virus and parapox virus ORF D1701 were boiled in 50 µl of sample buffer. 50 µl portions of the samples were applied to each gel slot, representing a viral quantity of 10 µg per slot. Next the viral proteins were separated electrophoretically at 50 V and 20–30 mA for approx. 16 hours. Two molecular weight standards (MW SDS-70L kit and MW SDS-200 kit; manufactured by Sigma) were carried out concomitantly to identify the proteins, and these covered a range from 14,300 to 205,000 daltons. After separation, the lanes with the marker proteins and one lane, on which viral proteins had been separated, were cut off and silver-stained to localize the marker bands. The remainder of the protein gel was meanwhile kept in electrode buffer at 4° C. Using the silver-stained gel strip as a guide, all the protein bands were excised by scalpel from the molecular weight range around 14 kD. In each case, six such gel pieces (approx. 0.5 ml in volume) were then put in turn into wells provided for them in an Extraphor electrophoretic concentrator (made by Pharmacia LKB). The various protein bands were eluted from the gel bits for 30 minutes at room temperature and 100 V, and at the same time precipitated in the "high-salt buffer". The precipitated proteins were removed, combined and centrifuged for 30 minutes at 10,000 rpm. After resuspending the sediment in 1 ml PBS and dialysis overnight at 4° C. in dialysis tubing with an exclusion molecular weight of 8 kD, the preparations were centrifuged for 30 minutes at 10,000 rpm under sterile conditions and then processed as described above to prepare the multipotent paramunity inducers.

EXAMPLE 9

Various poxvirus components were subjected to a VSV test to compare their paramunizing properties. The poxvirus components PIND-AVI and PIND-ORF, and the ORF protein 4D9 purified from cell cultures using immunity affinity chromatography, were compared with the recombined poxvirus PIND-AVI+ORF 4D9, into which the DNA section coding for the ORF 4D9 polypeptide had been introduced by homologous recombination. As can be taken from Table 4, the effect of the multipotent paramunity inducer was markedly enhanced over the effect of the individual components.

EXAMPLE 10

Figure 2:
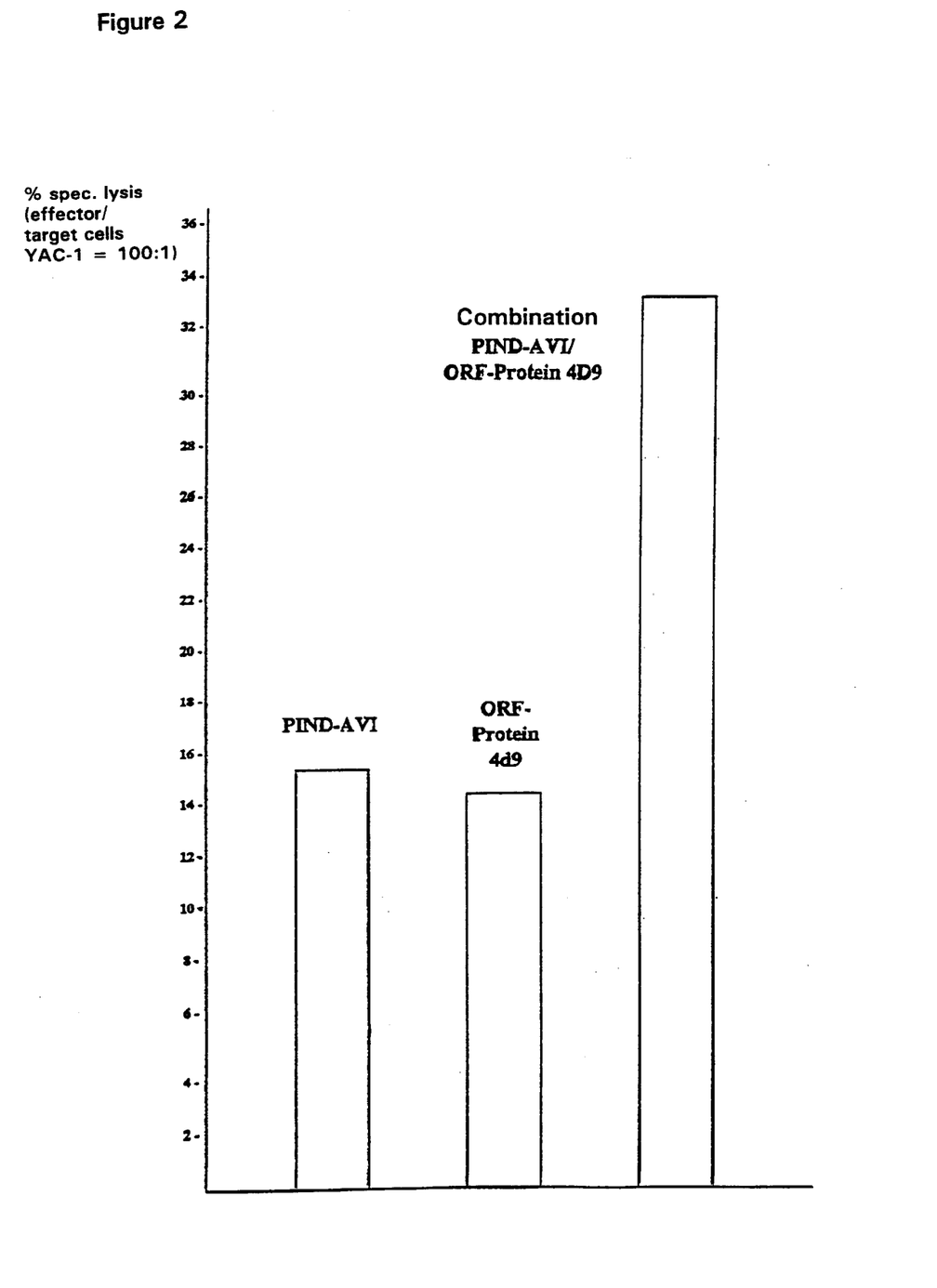
FIG. 2 shows the potentiating effect of an inventive combination of poxvirus components ORF protein 4D9 and PIND-AVI as compared with the effect of the two individual components on the NK cell (natural killer cell) activity in the chromium-51 release test. The values indicated correspond to the mean of two different assays. The test procedure used is described in the literature reference Mayr 1986 cited above.

The potentiating effect of the combined multipotent paramunity inducers as compared with the effect of the individual components was demonstrated in the chromium-51 release test; see Mayr et al., 1986, ibid. The comparison related to the poxvirus components PIND-AVI and the ORF protein 4D9 (the latter having been purified from cell supernatants of cells previously infected with parapox virus ORF D1701) with a combination of PIND-AVI and ORF protein 4D9. FIG. 2 shows the results obtained.

INDICATIONS RELATING TO A DEPOSITED MICROORGANISM (PCT Rule 13bis)

A. The indications made below relate to the microorganism referred to in the description
on page 9, line 18

B. IDENTIFICATION OF DEPOSIT — Further deposits are identified on an additional sheet ☐

Name of depositary institution

European Collection of Animal Cell Culture (ECACC)

Address of depositary institution (including postal code and country)

Centre for Applied Microbiology and Research
Porton Down
Salisbury, SP4 OJG
United Kingdom

| Date of deposit | Accession Number |
|---|---|
| January 27, 1994 | V94012706 |

C. ADDITIONAL INDICATIONS (leave blank if not applicable)  This information is continued on an additional sheet ☐

Parapoxvirus Strain ORF D 1701

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

For receiving Office use only
☒ This sheet was received with the international application Authorized officer
C.A.J.A. PASCHE For International Bureau use only
☐ This sheet was received by the International Bureau on:

Authorized officer

ACCESSION FORM FOR VIRUS DEPOSITS

ECACC USE ONLY

Date received: ................ Virus Assay ................

Depositor No. ................ Contamination test ................

Lab. Ref. No. ................

DEPOSITOR INFORMATION

Name of depositor MMMyr. Anton

Institute ................

Department ................

Address Prof. Dr. Dr. h.c. mult. Anton Mayr
Böckmayrstraße 9
80992 München

VIRUS INFORMATION

Abbreviated virus name AVP gallinae

Name in full Avipoxvirus gallinae

Strain HP1 - 444

Serological type APV gallinae

Normal host chicken

Normal vector ---- highly attenuated strain !!!

PROPAGATION AND ASSAY CELL CULTURE INFORMATION

Identification code strain HP1

Species and strain ................

Name in full AVP gallinae strain HP1

Organ/Tissue CEF (chicken embryo fibroblast cell culture, primary)

CULTURE CONDITIONS FOR VIRUS ASSAY

Medium (give full details on additional sheet if special formulation) MEM

Sodium bicarbonate (mg/l) 0.17% %/serum and type none pH 7.2 - 7.4 Temperature 37°C Gaseous phase none Any additional supplements none Technique for routine assay cultivation in CEF Sterility checks already performed:

| | | | | | |
|---|---|---|---|---|---|
| Bacteria | Yes neg. | No ...... | Fungi | Yes neg. | No ...... |
| Mycoplasma | Yes neg. | No ...... | Vir us | Yes neg. | No ...... |

Known contaminants none

VIRUS STORAGE CONDITIONS

Composition of medium MEM without serum Cell concentration ---

Method storage at 4°C for at least 10 years (virus lyophilized)

ACCESSION FORM FOR VIRUS DEPOSITS

ECACC USE ONLY

Date received: .....................................................  Virus Assay .............................................................

Depositor No. ....................................................  Contamination test ................................................

Lab. Ref. No. .....................................................

DEPOSITOR INFORMATION

Name of depositor ..... MAYR, Anton .........................

Institute ...............................................................

Department ..........................................................

Address ...... Prof. Dr. Dr. h.c. mult. Anton Mayr
Böckmeyrstraße 9
80992 München

VIRUS INFORMATION

Abbreviated virus name PPV ovis ORF D1701

Name in full Parapoxvirus ovis ORF D1701

Strain ORF D1701 - 135

Serological type PPV ovis

Normal host .... sheep

Normal vector ......... ----- highly attenuated virus strain !!!!

PROPAGATION AND ASSAY CELL CULTURE INFORMATION

Identification code ..... ORF D 1701 ..................  Name in full Parapoxvirus ovis ORF D 1701

Species and strain .................................................  Organ/Tissue ... MA cell strain(monkey kidney)

CULTURE CONDITIONS FOR VIRUS ASSAY

Medium (give full details on additional sheet if special formulation) MEM

Sodium bicarbonate (mg/l) ......... 0.17% ............................ %/serum and type ..none..................

pH  7.2 - 7.4 ............ Temperature ... $37^0$C ........................ Gaseous phase .... none.................

Any additional supplements ......... none.............................................................................

Technique for routine assay .. cultivation in MA cell strain .................................................

Sterility checks already performed:

Bacteria    Yes neg. No ..........    Fungi    Yes neg.: No ..........

Mycoplasma  Yes neg.: No ..........    Virus    Yes neg. No ..........

Known contaminants ......... none ............................................................................

VIRUS STORAGE CONDITIONS

Composition of medium MEM without serum ............ Cell concentration ... ----..................

Method  storage at $4^0$ C for at least 10 years (virus material lyophilized)

ACCESSION FORM FOR VIRUS DEPOSITS

ECACC USE ONLY

Date received: ..................................................   Virus Assay ..................................................

Depositor No. ..................................................   Contamination test ..................................................

Lab. Ref. No. ..................................................

DEPOSITOR INFORMATION

Name of depositor MAYR, Anton

Institute ..................................................

Department ..................................................

Address Prof. Dr. Dr. h.c. mult. Anton Mayr
Böckmeyrstraße 9
80992 München

VIRUS INFORMATION

Abbreviated virus name ...Vacciniavirus MVA

Name in full ...OPV commune strain MVA

Strain MVA (Modified Vacciniavirus Ankara)

Serological type ......OPV commune

Normal host ...human

Normal vector .........---- highly attenuated virus material !!!

PROPAGATION AND ASSAY CELL CULTURE INFORMATION

Identification code ...MVA

Species and strain ..................................................

Name in full ...OPV commune MVA

Organ/Tissue ...CEF (primary chicken embryo cell culture)

CULTURE CONDITIONS FOR VIRUS ASSAY

Medium (give full details on additional sheet if special formulation)   MEM

Sodium bicarbonate (mg/l) ...0.17%   %/serum and type ......none pH ......7.2 - 7.4   Temperature ...$37^0$C   Gaseous phase ...none Any additional supplements ...none Technique for routine assay ...cultivation in CEF Sterility checks already performed:

| | | | | |
|---|---|---|---|---|
| Bacteria | Yes .negative No ........ | | Fungi | Yes ...neg.... No ........ |
| Mycoplasma | Yes .neg..... No ........ | | Virus | Yes ...neg.... No ........ |

Known contaminants ..........none

VIRUS STORAGE CONDITIONS

Composition of medium ...MEM without serum............ Cell concentration ......---

Method ...storage at $4^0$C for at least 10 years (virus material lyophliiedd)

ACCESSION FORM FOR VIRUS DEPOSITS

ECACC USE ONLY

Date received: .....................................  Virus Assay .....................................

Depositor No. ....................................  Contamination test ...........................

Lab. Ref. No. ....................................

DEPOSITOR INFORMATION

Name of depositor ..MAYR, Anton..............

Institute ..............................................

Department ..........................................

Address ..Prof. Dr. Dr. h.c. mult. Anton Mayr..
............Bockmeyrstraße 9................
............80992 München...................

VIRUS INFORMATION

Abbreviated virus name ..AVP serinae KP1..

Name in full ..Avipoxvirus serinae (canary) KP1

Strain ..KP1 - 535..............................

Serological type ..AVP serinae..............

Normal host ..canary..........................

Normal vector ..-----..........................

highly attenuated strain !!!

PROPAGATION AND ASSAY CELL CULTURE INFORMATION

Identification code ..KP1.......................

Species and strain ..............................

Name in full ..AVP serinae KP1..............

Organ/Tissue ..CEF (primary chicken embryo cell culture)

CULTURE CONDITIONS FOR VIRUS ASSAY

Medium (give full details on additional sheet if special formulation)  MEM

Sodium bicarbonate (mg/l) ..0.17%..............  %/serum and type ..none..............

pH ..7.2 - 7.4..  Temperature ..37° C..  Gaseous phase ..none..

Any additional supplements ..none..............

Technique for routine assay ..cultivation in CEF..

Sterility checks already performed:

| | | | | |
|---|---|---|---|---|
| Bacteria | Yes neg. No | | Fungi | Yes ..neg... No |
| Mycoplasma | Yes neg. No | | Virus | Yes ..neg... No |

Known contaminants ..none..............

VIRUS STORAGE CONDITIONS

Composition of medium ..MEM..............  Cell concentration ..---..

Method ..storage at 4°C for at least 10 years (virus material lyophilized)..

TABLE 1

| pre-paration dilution | efficacy index (mean of at least 2 tests) | | | | | |
|---|---|---|---|---|---|---|
| | PIND-AVI | PIND-ORF | combination of AVI/ORF | BCG | leva-misole | C. parvum |
| 1:4 | 77 | 93 | 90 | 21 | toxic | |
| 1:8 | 47 | 78.5 | 96 | 0 | 0 | toxic |
| 1:16 | 40.5 | 76.5 | 86 | 0 | 0 | 22 |
| 1:32 | 8.5 | 63 | 70 | — | 0 | 21 |
| 1:64 | 0 | 27 | 56 | — | 0 | 0 |
| 1:128 | 0 | 1.5 | 27.5 | — | 0 | 0 |
| 1:256 | 0 | 0 | 4 | — | — | 0 |

TABLE 2

| | UE/ml in the VSV test | | |
|---|---|---|---|
| virus strain | wild type | early attenuation passage | late attenuation passage |
| vaccinia virus MVA | <20 | ≦40 | 160–320 |
| avipox virus HP1 | <20 | ≦40 | 80–160 |
| canarypox virus KP-1 | <20 | ≦40 | 160–320 |
| parapox virus ORF D1701 | <20 | ≦40 | 320–640 |

TABLE 3

| virus species | strain | Inf. titer $-\log_{10}$ (MOI = 1) | antiviral activity of mononuclear leukocytes in E.U./ml | | |
|---|---|---|---|---|---|
| | | | human | sheep | pig |
| vaccinia virus wild type | Copenhagen | 8.75 | <40 | <40 | <40 |
| early passage | Elstree Bern | 7.4 7.05 | <40 <40 | <40 <40 | n.d. <40 |
| attenuated | MVA | 8.05 | 160–320 | 80 | 320 |
| avipox virus early passage | HP1 | 7.0 | <40 | <40 | <40 |
| attenuated | | 6.3 | 1280 | 320 | 80 |
| parapox wild-type | D1701 | 6.5 | <40 | <40 | <40 |

TABLE 3-continued

| virus species | strain | Inf. titer $-\log_{10}$ (MOI = 1) | antiviral activity of mononuclear leukocytes in E.U./ml | | |
|---|---|---|---|---|---|
| | | | human | sheep | pig |
| virus attenuated | | 7.3 | 320–640 | 160 | 160 |

TABLE 4

| Inducer type | EU/ml (1:8 predilution) |
|---|---|
| PIND-AVI | 160–320 |
| PIND-ORF | 320–640 |
| ORF-Protein 4D9 | 40–80 |
| recombined paramunity inducer PIND-AVI + ORF 4D9 | 1280–2560 |

What is claimed is:

1. A paramunity inducer comprising a plurality of poxvirus components obtainable from different poxvirus strains with paramunizing properties, wherein the poxvirus are selected from the group of genera consisting of avipoxvirus, orthopoxvirus and parapoxvirus, wherein the poxvirus components are virus envelopes or aberrant forms of virus envelopes that have been obtained from poxviruses.

2. The paramunity inducer according to claim 1, wherein the poxvirus are inactivated.

3. The paramunity inducer according to claim 2, wherein the poxviruses are inactivated by treatment with 8-propiolactone in a pH range of 8 to 9.

4. The paramunity inducer according to claim 1, wherein the poxvirus components are from recombinant viruses.

5. The paramunity inducer according to claim 1, wherein the poxviruses are freshly isolated.

6. A pharmaceutical composition comprising a plurality of poxvirus components obtainable from different poxvirus strains with paramunizing properties, wherein the poxvirus strains are freshly isolated.

7. The pharmaceutical composition according to claim 6, wherein the poxvirus strains are inactivated.

8. The pharmaceutical composition according to claim 6, wherein the poxvirus strains are recombinant viruses.

* * * * *